United States Patent
Schmidt et al.

(10) Patent No.: US 12,173,163 B2
(45) Date of Patent: Dec. 24, 2024

(54) PIGMENT MIXTURE

(71) Applicant: MERCK PATENT GMBH, Darmstadt (DE)

(72) Inventors: Christoph Schmidt, Kriftel (DE); Carsten Plueg, Muehltal (DE); Uwe Lenz, Zwingenberg (DE); Sabine Schoen, Herten (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/255,227

(22) Filed: Jan. 23, 2019

(65) Prior Publication Data

US 2019/0225813 A1 Jul. 25, 2019

(30) Foreign Application Priority Data

Jan. 23, 2018 (EP) .................................. 18153057

(51) Int. Cl.
| | | |
|---|---|---|
| *C09C 1/00* | (2006.01) | |
| *A61K 8/02* | (2006.01) | |
| *A61K 8/19* | (2006.01) | |
| *A61K 8/25* | (2006.01) | |
| *A61K 8/26* | (2006.01) | |
| *A61K 8/29* | (2006.01) | |
| *A61Q 1/02* | (2006.01) | |
| *C09D 17/00* | (2006.01) | |
| *A61Q 1/12* | (2006.01) | |

(52) U.S. Cl.
CPC .......... *C09C 1/0051* (2013.01); *A61K 8/0262* (2013.01); *A61K 8/19* (2013.01); *A61K 8/25* (2013.01); *A61K 8/26* (2013.01); *A61K 8/29* (2013.01); *A61Q 1/02* (2013.01); *C09C 1/0021* (2013.01); *C09C 1/0081* (2013.01); *C09D 17/008* (2013.01); *A61K 2800/412* (2013.01); *A61K 2800/436* (2013.01); *A61K 2800/592* (2013.01); *A61Q 1/12* (2013.01); *C01P 2004/51* (2013.01); *C01P 2006/63* (2013.01); *C01P 2006/64* (2013.01); *C09C 2200/1004* (2013.01); *C09C 2200/102* (2013.01); *C09C 2200/1062* (2013.01); *C09C 2200/1087* (2013.01); *C09C 2200/301* (2013.01); *C09C 2220/106* (2013.01)

(58) Field of Classification Search
CPC ........ A61K 2800/412; A61K 2800/436; A61K 2800/592; A61K 8/0262; A61K 8/19; A61K 8/25; A61K 8/26; A61K 8/29; A61Q 1/02; A61Q 1/12; C01P 2004/51; C01P 2006/63; C01P 2006/64; C09C 1/0021; C09C 1/0051; C09C 1/0081; C09C 2200/1004; C09C 2200/102; C09C 2200/1062; C09C 2200/1087; C09C 2200/301; C09C 2220/106; C09D 17/008

See application file for complete search history.

(56) References Cited

U.S. PATENT DOCUMENTS

| | | | | |
|---|---|---|---|---|
| 6,472,455 | B1 * | 10/2002 | Bleikolm | C09C 1/0021 523/160 |
| 7,993,444 | B2 | 8/2011 | Fuller et al. | |
| 8,016,934 | B2 | 9/2011 | Misaki et al. | |
| 8,486,189 | B2 | 7/2013 | Hollman et al. | |
| 8,926,746 | B2 * | 1/2015 | Wakamiya | C09D 7/61 106/415 |
| 9,089,493 | B2 | 7/2015 | Elsbrock et al. | |
| 2007/0065381 | A1 * | 3/2007 | Elsbrock | A61K 8/29 424/63 |
| 2008/0210133 | A1 * | 9/2008 | Roesler | C09D 5/36 106/482 |
| 2013/0118380 | A1 | 5/2013 | Roesler et al. | |
| 2014/0271740 | A1 | 9/2014 | Ballesteros et al. | |
| 2017/0290750 | A1 | 10/2017 | Hamm et al. | |

FOREIGN PATENT DOCUMENTS

| | | |
|---|---|---|
| CN | 107286706 B | 4/2021 |
| EP | 1928400 B1 | 8/2016 |
| JP | 2002527563 A | 8/2002 |
| JP | 2006193738 A | 7/2006 |
| JP | 2007508447 A | 4/2007 |
| JP | 2009503205 A | 1/2009 |
| JP | 2010530467 A | 9/2010 |
| JP | 2014189514 A | 10/2014 |
| KR | 20050094854 A | 9/2005 |
| KR | 20080032219 A | 4/2008 |
| WO | 07031970 A2 | 3/2007 |

OTHER PUBLICATIONS

Search report in corresponding EP19152699.5 dated Jun. 28, 2019 (pp. 1-7).
Office Action in corresponding Japanese Patent Application No. 2019-009110 dated Jun. 29, 2022 (pp. 1-2) and english translation thereof (pp. 1-2).
Office Action in corresponding CN application 201910056152.6 dated Sep. 15, 2022 (pp. 1-9).
Office action in corresponding JP application 2019009110 dated Mar. 27, 2023 (2 Pages) and English machine translation thereof (1 page).
Search report in corresponding Korean appln No. 2019-0007816 dated Dec. 13, 2023 (pp. 1-6).

* cited by examiner

*Primary Examiner* — Shuangyi Abu Ali
(74) *Attorney, Agent, or Firm* — MILLEN, WHITE, ZELANO & BRANIGAN, P.C.; Ryan R. Pool

(57) ABSTRACT

A pigment mixture comprising at least two or three interference pigments of different interference colours selected from the colours red, green and blue, suitable for use in paints, coatings, printing inks, security printing inks, plastics, ceramic materials, glasses and in the preparation of pigment preparations, dry preparations and in particular cosmetic formulations.

16 Claims, No Drawings

PIGMENT MIXTURE

The present invention relates to a pigment mixture comprising at least two or three interference pigments of different interference colours selected from the colours red, green and blue, and to the use thereof in paints, coatings, printing inks, security printing inks, plastics, ceramic materials, glasses and for the preparation of pigment preparations and dry preparations and in particular in cosmetic formulations.

In decorative cosmetics, optical neutralisation of skin irregularities and/or undesired colour shades of the skin is an important area of application. The aim here is to provide the skin, in particular in the facial area, with a uniform appearance and an individually desired hue without diminishing the natural appearance.

In many cases, classical absorption pigments are used for this purpose, but these have the disadvantage of hiding the skin in the manner of a mask.

WO 2007/031970 describes skin-care compositions which comprise interference pigments which have pairs of complementary colours. The use of complementary pigment pairs only enables the colour intensity to be controlled in a very narrow range along a colour curve. However, in order to cover the requisite colour range for use on the skin, WO 2007/031970 additionally teaches that four interference pigments in the form of two complementary red-green and blue-yellow colour pairs are necessary. This procedure has the disadvantage that the colour of the formulation cannot be set freely as desired. In particular, the mutual colour extinction of the complementary colour pairs makes the setting of a particular colour and colour intensity for a particular skin type very difficult or even impossible.

The object of the present invention is therefore to find a system comprising few pigments which enables any individually desired hue and any colour intensity to be set over a wide hue range, so that, for example in cosmetics, skin irregularities can be neutralised without the brightness of the appearance being impaired by colour extinction.

Surprisingly, it has been found that, through the use of red, green and blue interference pigments which are particularly suitable in terms of colour, the number of requisite interference colours can be reduced to two or three and at the same time the band width of achievable hues and colour intensities is significantly increased compared with the prior art and can be set individually. This enables the cosmetic formulation to be matched to any skin type in a simple manner.

The present invention thus relates to a pigment mixture comprising two or three interference pigments which each have different interference colours, where the interference colours are selected from the colours red, blue and green and are defined as follows in the CIE L*a*b* colour space:
  red interference pigment: a≥25 and b≥0,
  blue interference pigment: −20≤a≤40 and b≤−50
  green interference pigment: a≤−15 and b≥0.

The invention furthermore relates to the use of the pigment mixture according to the invention in paints, coatings, preferably in industrial and automobile paints, printing inks, security printing inks, plastics, ceramic materials, glasses, as tracer, as filler and in particular in cosmetic formulations. The pigments according to the invention are furthermore also suitable for the preparation of pigment preparations and for the preparation of dry preparations, such as, for example, granules, pearlets, chips, pellets, sausages, briquettes, etc. The dry preparations are used, in particular, in printing inks and in cosmetics.

The suitable interference pigments are characterised by the following properties in the CIE L*a*b* colour space:

The red interference pigment has the following a and b values in the CIE L*a*b* colour space:
  a≥25 and b≥0, preferably a≥30 and b≥5, in particular a≥35 and b≥5.

The blue interference pigment has the following a and b values in the CIE L*a*b* colour space:
  −20≤a≤40 and b≤−50, preferably −15≤a≤30 and b≤−60, in particular −10≤a≤20 and b<−65.

The green interference pigment has the following a and b values in the CIE L*a*b* colour space:
  a≤−15 and b≥0, preferably a≤−20 and b≥15, in particular a≤−25 and b≥20.

The pigment mixture according to the invention can comprise
  a red interference pigment and a green interference pigment or
  a red interference pigment and a blue interference pigment or
  a green interference pigment and a blue interference pigment or
  a red interference pigment, a blue interference pigment and a green interference pigment,
where the interference pigments must satisfy the above-mentioned conditions for the a and b values with their interference colours.

The present invention enables golden hues to be achieved with a red, green and/or blue effect pigment. A gold-coloured effect pigment is therefore not necessary, but can additionally be used in order to achieve particular desired hues.

Preferred mixtures of interference pigments comprising at least two interference pigments from the group red, green and blue interference pigment are those in which the individual pigments satisfy the following CIE L*a*b* colour ranges:
  red interference pigment: a≥30 and b≥5, blue interference pigment −15≤a≤30 and b<−60, green interference pigment: a≤−20 and b≥15.

Very particularly preferred pigment mixtures comprise at least two interference pigments which fall into the following CIE L*a*b* colour ranges:
  red interference pigment: a≥35 and b≥5,
  blue interference pigment: −10≤a≤20 and b<−65 and/or
  green interference pigment: a≤−25 and b≥20.

The red, green and blue interference pigments can be mixed with one another in any ratio depending on the desired colour and colour intensity.

Preferred mixing ratios (=amount ratios) of the red, green and/or blue interference pigments are shown below:
  red interference pigment+green interference pigment: 7:3 and below, preferably 3:7, in particular 1:1;
  red interference pigment+blue interference pigment: 2:1 and above, preferably 10:1, in particular 20:1;
  blue interference pigment+green interference pigment: 1:2 and below, preferably 1:10, in particular 1:20;
  red interference pigment+green interference pigment+ blue interference pigment: 2:2:1 and above, preferably 5:5:1, in particular 10:10:1

The colour intensity and hue of the four colours red/green/blue/gold of the pigment mixture can be set specifically through the selected mixing ratio of the two or three interference pigments.

Interference pigments have been described many times in the literature and are known to the person skilled in the art. Interference pigments which are particularly suitable for the pigment mixture according to the invention are based on flake-form substrates. Suitable flake-form substrates for the interference pigments are on the one hand opaque flake-form substrates and on the other hand transparent flake-form substrates. Preferred flake-form substrates are phyllosilicates. Particularly suitable are natural or synthetic mica, talc, kaolin, flake-form $Fe_2O_3$, $Fe_3O_4$, $Al_2O_3$, BiOCl, glass, $SiO_2$, $TiO_2$, BN, oxynitride, nitride or graphite flakes, pearl essence, synthetic support-free flakes or other comparable materials. It is also possible to use interference pigments based on different substrates in the pigment mixture according to the invention.

Particularly preferred interference pigment mixtures are based on
- mica flakes+$SiO_2$ flakes
- mica flakes+$Al_2O_3$ flakes
- mica flakes+glass flakes
- mica flakes+$TiO_2$ flakes
- mica flakes+oxynitride flakes
- mica flakes+nitride flakes
- mica flakes+pearl essence
- mica flakes+graphite flakes
- mica flakes+BiOCl
- $SiO_2$ flakes+$Al_2O_3$ flakes
- glass flakes+$SiO_2$ flakes.

Particular preference is given to interference pigments based on natural mica flakes, synthetic mica flakes, coated and uncoated glass flakes, $Al_2O_3$ flakes, $SiO_2$ flakes and glass flakes. The coated glass flakes are preferably glass flakes which have been covered with a $SiO_2$ layer. The mica flakes can likewise be covered with a thin layer (<10 nm) of $SiO_2$ or $Al_2O_3$ before the covering with the interference layer.

If the interference pigments are based on $Al_2O_3$ flakes, this is preferably alpha-aluminium oxide. The $Al_2O_3$ flakes may be doped or undoped. If they are doped, the dopant is preferably selected from the group $TiO_2$, $ZrO_2$, $SiO_2$, $In_2O_3$, $SnO_2$ and ZnO and combinations thereof. The proportion of the doping based on the aluminium oxide is preferably 0.01-5% by weight. In a preferred embodiment, the aluminium oxide flake contains only one dopant, in particular $TiO_2$, ZnO or $ZrO_2$.

The size of the flake-form substrates is not crucial per se and can be matched to the particular application. In general, the flake-form substrates have a thickness between 0.05 and 1.5 µm, in particular between 0.1 and 1 µm. The size in the other two dimensions is usually between 1 and 250 µm, preferably between 2 and 200 µm and in particular between 5 and 60 µm. It is also possible to employ substrates of different particle size. Particular preference is given to a mixture of mica fractions of mica N (10-60 µm), mica F (5-20 µm) and/or mica M (<15 µm). Preference is furthermore given to N and S fractions (10-130 µm) and F and S fractions (5-130 µm).

Interference pigments which are particularly suitable for the pigment mixture according to the invention are based on flake-form substrates which have been coated with one or more interference layers, preferably one or more metal oxides, on the surface, i.e. are completely enveloped. Particular preference is given to interference pigments which are based on flake-form substrates and have a surface coating of $TiO_2$ and/or $Fe_2O_3$ or a sequence using two or more oxides from the series of, for example, $TiO_2$, $SiO_2$, $Fe_2O_3$, $Cr_2O_3$, $ZrO_2$, $Al_2O_3$, $SnO_2$, where at least one oxide in the sequence should be highly refractive and should have a refractive index of 1.8.

If the interference layer consists of $TiO_2$ or comprises $TiO_2$, the titanium dioxide can be in the rutile or anatase modification. The titanium dioxide is preferably in the form of rutile.

Particular preference is given to interference pigments having red, green and blue interference colours which have a particle size of 2-70 µm, preferably 10-60 µm, and preferably 4-28 µm (F fraction) and comprise natural or synthetic mica as substrate. Preference is furthermore given to red and green interference pigments which have a yellow-tinged hue. This "yellow tinge" is reflected in the b value in the CIE L*a*b* colour space, i.e. the b value must be >0. By mixing a defined red interference pigment with a defined green interference pigment, each with a yellow tinge, it is possible to establish red, green and gold hues of different colour tonality and colour intensity.

In order to cover all hues in the applications, preferably in the cosmetic formulations, it is furthermore advisable to set the particle sizes and the particle size distribution of the interference pigments in the pigment mixture according to the invention.

The red interference pigments preferably have a particle size distribution (determined in accordance with Malvern, Mastersizer 2000) of
$D_{10}$=<12 µm, preferably <10 µm, in particular <7 µm
$D_{50}$=<25 µm, preferably <15 µm, in particular <12 µm
$D_{90}$=<45 µm, preferably <20 µm, in particular <17 µm.

The green interference pigments preferably have a particle size distribution (determined in accordance with Malvern) of
$D_{10}$=<12 µm, preferably <10 µm, in particular <7 µm
$D_{50}$=<25 µm, preferably <15 µm, in particular <12 µm
$D_{90}$=<45 µm, preferably <20 µm, in particular <17 µm.

The blue interference pigments preferably have a particle size distribution (determined in accordance with Malvern) of
$D_{10}$=<12 µm, preferably <10 µm, in particular <7 µm
$D_{50}$=<25 µm, preferably <15 µm, in particular <12 µm
$D_{90}$=<45 µm, preferably <20 µm, in particular <17 µm.

Very particularly preferred interference pigments have a particle size in the range from 5 to 30 µm, with a $D_{90}$ value of <25 µm and a $D_{50}$ value of <15 µm. The $D_{10}$ value is preferably <10 µm.

In order to improve the result further, additional silver interference pigments and/or absorption pigments may optionally be added to the cosmetic formulation.

The invention also relates to a process for the preparation of the pigment mixture according to the invention, which is distinguished by the fact that two or three interference pigments having different interference colours and defined a and b values in the CIE L*a*b* colour system are mixed with one another.

Suitable red, green and blue interference pigments having the defined CIE L*a*b* colour values can easily be prepared by covering the surface of the flake-form substrates with one or more highly refractive interference layer(s), preferably metal oxide layer(s).

The metal oxide layer(s) are preferably applied by wet-chemical methods, where the wet-chemical coating methods developed for the preparation of pearlescent pigments can be used; methods of this type are described, for example, in U.S. Pat. Nos. 3,087,828, 3,087,829, 3,553,001, DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017, DE 196 18 568, EP 0 659 843, or in further patent documents and other publications known to the person skilled in the art.

A SiO$_2$ layer is preferably applied using the method described in DE 196 18 569. The SiO$_2$ layer is preferably produced using sodium water-glass solution or potassium water-glass solution.

In the case of wet coating, the substrate flakes are suspended in water, and one or more hydrolysable metal salts are added at a pH suitable for hydrolysis which is selected so that the metal oxides or metal oxide hydrates are precipitated directly onto the flakes without secondary precipitations occurring. The pH is usually kept constant by simultaneous metered addition of a base and/or acid. The pigments are subsequently separated off, washed and dried and optionally calcined, where the calcination temperature can be optimised with respect to the coating present in each case. In general, the calcination temperatures are between 250 and 1000° C., preferably between 350 and 900° C. If desired, the pigments can be separated off, dried and optionally calcined after application of individual coatings and then re-suspended again for the precipitation of the further layers.

Furthermore, the coating can also be carried out by gas-phase coating in a fluidized-bed reactor, where, for example, the methods proposed in EP 0 045 851 and EP 0 106 235 for the preparation of pearlescent pigments can be used correspondingly.

The hue of the interference pigments can be varied in broad limits by different choice of the coating amounts or of the resultant layer thicknesses. Fine tuning for a particular hue can be achieved beyond the pure choice of amounts by approaching the desired colour under visual or metrological control In order to increase the light, water and weather stability, it is frequently advisable, depending on the area of application, to subject the pigment mixture to post-coating or post-treatment. Suitable post-coatings or post-treatments are, for example, the methods described in German patent 22 15 191, DE-A 31 51 354, DE-A 32 35 017 or DE-A 33 34 598. This post-coating further increases the chemical and photochemical stability or simplifies handling of the pigment mixture, in particular incorporation into various media. In order to improve the wettability, dispersibility and/or compatibility with the user media, functional coatings of Al$_2$O$_3$ or ZrO$_2$ or mixtures thereof can be applied to the pigment surface. Furthermore, organic post-coatings are possible, for example with silanes, as described, for example, in EP 0090259, EP 0 634 459, WO 99/57204, WO 96/32446, WO 99/57204, U.S. Pat. Nos. 5,759,255, 5,571, 851, WO 01/92425 or in J. J. Ponjeé, Philips Technical Review, Vol. 44, No. 3, 81 ff., and P. H. Harding J. C. Berg, J. Adhesion Sci. Technol. Vol. 11 No. 4, pp. 471-493.

Coating(s) in this patent application are taken to mean complete covering/enveloping of the flake-form substrates.

The pigment mixture according to the invention is compatible with a multiplicity of colour systems, preferably from the area of paints, coatings and printing inks. For the preparation of printing inks for, for example, gravure printing, flexographic printing, offset printing or offset overprint varnishing, a multiplicity of binders, in particular water-soluble types, is suitable, as marketed, for example, by the BASF, Marabu, Proöll, Sericol, Hartmann, Gebr. Schmidt, Sicpa, Aarberg, Siegwerk, GSB-Wahl, Follmann, Ruco or Coates Screen INKS GmbH companies. The printing inks can be built up on a water basis or solvent basis.

The pigment mixture according to the invention is particularly suitable for decorative cosmetics and for personal care applications, such as, for example, nail varnishes, lipsticks, compact powders, gels, lotions, soaps, toothpastes, body lotions, emulsions, soaps, shampoos, BB creams, CC creams, makeup, foundations, mascara, hair, eyelash and eyebrow products, etc., but also in paints, in industrial coatings and powder coatings, as well as in plastics and in ceramics.

In decorative cosmetics, the pigment mixture according to the invention is preferably employed in concentrations of 0.5-25% by weight, in particular 1-20% by weight, and very particularly preferably 1-10% by weight, based on the formulation. In the case of cosmetic formulations for personal care applications, the pigment mixture according to the invention is preferably employed in concentrations of 0.1-5% by weight, and very particularly preferably 0.5-4% by weight, based on the formulation.

Since the pigment mixture according to the invention enables any colour to be set for any skin type, the pigment mixture is particularly suitable for neutralising skin irregularities and can therefore preferably be used in medical covering ointments, contour sticks, makeups, foundations or concealers. The cosmetic formulations for use as skin corrector preferably comprise the pigment mixture according to the invention in amounts of 0.5-25% by weight, in particular 1-20% by weight, based on the formulation.

It goes without saying that, for the various applications, the pigment mixture according to the invention can also advantageously be employed in a mixture with, for example, metal-effect pigments, for example based on iron flakes or aluminium flakes;
absorption pigments;
multilayered effect pigments (preferably comprising 2, 3, 4, 5 or 7 layers) based on metal-oxide-coated synthetic mica flakes, natural mica flakes, glass flakes, Al$_2$O$_3$ flakes, Fe$_2$O$_3$ flakes or SiO$_2$ flakes;
organic dyes;
organic pigments;
inorganic pigments, such as, for example, transparent and opaque white, coloured and black pigments;
flake-form iron oxides;
carbon black.

The pigment mixture according to the invention can be mixed in any ratio with commercially available pigments and/or further commercially available fillers.

Commercially available fillers which may be mentioned are, for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, boron nitride and physical or chemical combinations of the substances. There are no restrictions regarding the particle shape of the filler. In accordance with requirements, it can be, for example, flake-form, spherical or needle-shaped.

The pigment mixture according to the invention can of course also be combined in the formulations with any type of cosmetic raw materials and assistants. These include, inter alia, oils, fats, waxes, film formers, preservatives and assistants which generally determine the applicational properties, such as, for example, thickeners and rheological additives, such as, for example, bentonites, hectorites, silicon dioxides, Ca silicates, gelatines, high-molecular-weight carbohydrates and/or surface-active assistants, etc.

The formulation comprising the pigment mixture according to the invention can belong to the lipophilic, hydrophilic or hydrophobic type. In the case of heterogeneous formulations having discrete aqueous and non-aqueous phases, the pigment mixture according to the invention may be present in only one of the two phases in each case or may also be distributed over both phases.

The pH values of the formulations can be between 1 and 14, preferably between 2 and 11 and particularly preferably between 4 and 10. The concentrations of the pigment mixture according to the invention in the formulation are not subject to any limits. They can be—depending on the application—between 0.001 (rinse-off products, example shower gels) and 60%. The pigment mixture according to invention may furthermore also be combined with cosmetic active compounds. Suitable active compounds are, example, insect repellents, inorganic UV filters, such as, for example, $TiO_2$, UV A/BC protection filters (for example OMC, B3, MBC), including in encapsulated form, anti-ageing active compounds, vitamins and derivatives thereof (for example vitamin A, C, E, etc.), self-tanning agents (for example DHA, erythrulose, inter alia) and further cosmetic active compounds, such as, for example, bisabolol, LPO, ectoin, emblica, allantoin, bioflavonoids and derivatives thereof.

Organic UV filters are generally employed in an amount of 0.5-10% by weight, preferably 1-8% by weight, and inorganic UV filters are generally employed in an amount of 0.1-30% by weight, based on the cosmetic formulation.

The formulations may in addition comprise further conventional skin-protecting or skin-care active compounds, such as, example, aloe vera, avocado oil, coenzyme Q10, green tea extract also active compound complexes.

The present invention likewise relates to formulations, in particular cosmetic formulations, which, besides the pigment mixture according to the invention, comprise at least one constituent selected from the group of the absorbents, astringents, antimicrobial substances, antioxidants, antiperspirants, antifoaming agents, antidandruff active compounds, antistatics, binders, biological additives, bleaching agents, chelating agents, deodorising agents, emollients, emulsifiers, emulsion stabilisers, dyes, humectants, film formers, fillers, fragrances, flavours, insect repellents, preservatives, corrosion protection agents, cosmetic oils, solvents, oxidants, vegetable constituents, buffer substances, reducing agents, surfactants, propellant gases, opacifying agents, UV filters and UV absorbers, denaturing agents, aloe vera, avocado oil, coenzyme Q10, green tea extract, viscosity regulators, perfume and vitamins.

The invention also relates to the use of the pigment mixture according to the invention in paints, coatings, printing inks, security printing inks, plastics, ceramic materials, glazes, glasses, as tracer, in cosmetic formulations and for the preparation of pigment preparations and dry preparations.

The following examples are intended to explain the invention in greater detail, but without limiting it.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 18153057.7, filed Jan. 23, 2018, are incorporated by reference herein.

EXAMPLES

The a and b values of the individual interference pigments are determined using a STEAG ETA-Optik spectrometer as follows: a black-coated paint card is coated using a hand coater (gap width 500 μm) with a nitrocellulose lacquer which comprises 1.65 percent by weight of the interference pigment or pigment mixture in question.

After drying, the colour is measured below 95° using the above-mentioned measuring instrument at an angle of incidence of 75°. 90° is the perpendicular to the paint card.

Example 1

Preparation of a Red Interference Pigment having a High Yellow Content Based on Aluminium Oxide Flakes 100 g of $Al_2O_3$ flakes having a particle size of 5-30 μm ($D_{50}$=18 μm) are suspended in 1.6 l of demineralised water, and the suspension is warmed to 75° C. with vigorous stirring. A solution of 5 g of $SnCl_4 \times 5H_2O$ in 70 g of water is slowly metered into this suspension at pH=2. The pH is kept constant at 2 using 32% sodium hydroxide solution. The pH is then reduced to 1.8, and 820 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated $Al_2O_3$ flakes are then filtered off, washed and dried at 110° C. for 15 h. Finally, the pigment is calcined at 850° C. for 1 h.

The red interference pigment has the following a and b values:

| a: 48.55 | b: 18.37 |
| --- | --- |

Example 2

Preparation of a Red Interference Pigment having a High Yellow Content Based on Mica 100 g of natural mica having a particle size of 5-25 μm ($D_{50}$=11 μm) are suspended in 2 l of demineralised water, and the suspension is warmed to 75° C. with vigorous stirring. A solution of 3 g of $SnCl_4 \times 5H_2O$ in 100 g of water is slowly metered into this suspension at pH=2. The pH is kept constant at 2 using 32% sodium hydroxide solution. The pH is then reduced to 1.8, and 1100 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated mica pigment is then filtered off, washed and dried at 110° C. for 15 h. Finally, the pigment is calcined at 850° C. for 1 h.

The red interference pigment has the following a and b values:

| a: 40.64 | b: 13.41 |
| --- | --- |

Example 3

Preparation of a Blue Interference Pigment Based on Aluminium Oxide Flakes 100 g of $Al_2O_3$ flakes having a particle size of 5-30 µm ($D_{50}$=18 µm) are suspended in 1.6 l of demineralised water, and the suspension is warmed to 75° C. with vigorous stirring. A solution of 9.3 g of $SnCl_4 \times 5H_2O$ in 130 g of water is slowly metered into this suspension at pH=2. During this addition, the pH is kept constant at 2 using 32% sodium hydroxide solution. The pH is then reduced to 1.8, and 714 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated $Al_2O_3$ flakes are then filtered off, washed and dried at 110° C. for 15 h. Finally, the pigment is calcined at 850° C. for 1 h.

The blue interference pigment has the following a and b values:

| a: 2.61 | b: −59.75 |
|---|---|

Example 4

Preparation of a Blue interference Pigment Based on Mica 70 g of natural mica having a particle size of 1-20 µm ($D_{50}$=9 µm) are suspended in 1.4 l of demineralised water, and the suspension is warmed to 75° C. with vigorous stirring. A solution of 15 g of $SnCl_4 \times 5H_2O$ in 210 g of water is slowly metered into this suspension at pH=2. The pH is kept constant at 2 using 32% sodium hydroxide solution. The pH is then reduced to 1.8, and 1056 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated mica pigment is then filtered off, washed and dried at 110° C. for 15 h. Finally, the pigment is calcined at 850° C. for 1 h.

The blue interference pigment has the following a and b values:

| a: 12.44 | b: −82.11 |
|---|---|

Example 5

Preparation of a Green Interference Pigment Having a High Yellow Content Based on Aluminium Oxide Flakes 100 g of $Al_2O_3$ flakes having a particle size of 5-30 µm ($D_{50}$=18 µm) are suspended in 1.6 l of demineralised water, and the suspension is warmed to 75° C. with vigorous stirring. A solution of 5 g of $SnCl_4 \times 5H_2O$ in 100 g of water is slowly metered into this suspension at pH=2. The pH is kept constant at 2 using 32% sodium hydroxide solution. The pH is then reduced to 1.8, and 878 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated $Al_2O_3$ flakes are then filtered off, washed and dried at 110° C. for 15 h. Finally, the pigment is calcined at 850° C. for 1 h.

The green interference pigment has the following a and b values:

| a: −46.81 | b: 34.62 |
|---|---|

Example 6

Preparation of a Green Interference Pigment Having a High Yellow Content Based on Mica 70 g of natural mica having a particle size of 5-25 µm ($D_{50}$=11 µm) are suspended in 1.4 l of demineralised water, and the suspension is warmed to 75° C. with vigorous stirring. A solution of 2.1 g of $SnCl_4 \times 5H_2O$ in 70 g of water is slowly metered into this suspension at pH=2. During this addition, the pH is kept constant at 2 using 32% sodium hydroxide solution. The pH is then reduced to 1.8, and 1005 g of a 32% $TiCl_4$ solution are slowly metered in at this pH. The addition of the $TiCl_4$ solution is terminated when the desired colour end point has been reached. After termination of the $TiCl_4$ addition, the mixture is stirred for a further hour, and the coated mica pigment is then filtered off, washed and dried at 110° C. for 15 h. Finally, the pigment is calcined at 850° C. for 1 h.

The green interference pigment has the following a and b values:

| a: −32.89 | b: 35.18 |
|---|---|

Example 7

Preparation of a Green Interference Pigment Having a High Yellow Content Based on Glass Flakes 100 g of glass flakes having a particle size of 10-60 µm ($D_{50}$=22 µm) and an average thickness of 450 nm are suspended in 1.4 l of demineralised water, and the suspension is warmed to 75° C. with vigorous stirring. The pH is then increased to pH 8 using sodium hydroxide solution, and a solution of 38 g of sodium water-glass (13% of $SiO_2$) are metered in at this pH over the course of 90 min. During this addition, the pH is kept constant using hydrochloric acid (18% by weight of HCl). The pH is subsequently reduced to pH 2 over the course of 45 min., and a solution of 5 g of $SnCl_4 \times 5H_2O$ in 70 g of water is slowly metered in at this pH. During this addition, the pH is kept constant at 2 using 32% sodium hydroxide solution. The pH is then reduced to 1.6, and 997 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated glass flakes are then filtered off, washed and dried at 110° C. for 15 h. Finally, the pigment is calcined at 650° C. for 1 h.

The green interference pigment has the following a and b values:

| a: −35.28 | b: 37.11 |
|---|---|

Example 8

Preparation of a Red Interference Pigment Having a High Yellow Content Based on Synthetic Mica 100 g of synthetic mica having a particle size of 5-40 μm ($D_{50}$=17 μm) are suspended in 2 l of demineralised water, and the suspension is warmed to 75° C. with vigorous stirring. The pH is then adjusted to pH 2.5 using hydrochloric acid (18% by weight of HCl). 9 g of $AlCl_3$ solution (29% by weight of $AlCl_3$) are metered in at this pH over the course 2 min., and the mixture is stirred for a further 15 min. 233 g of $SnCl_4$ solution (2.1% by weight of $SnCl_4$) are slowly metered into this suspension at pH=1.7. The pH is kept constant at 1.7 using 32% sodium hydroxide solution. The pH is then reduced to 1.4 using hydrochloric acid, and 848 g of a 32% $TiCl_4$ solution are slowly metered in at this pH. During this addition, the pH is kept constant using 32% sodium hydroxide solution. The addition of the $TiCl_4$ solution is terminated when the desired colour end point has been reached. After termination of the $TiCl_4$ addition, the mixture is stirred for a further hour, and the coated mica pigment is then filtered off, washed and dried at 110° C. for 15 h. Finally, the pigment is calcined at 850° C. for 30 min.

The red interference pigment has the following a and b values:

| a: 52.71 | b: 17.24 |
|---|---|

Paint Example 1

A mixture of red interference pigment in accordance with Example 2 and green interference pigment in accordance with Example 6 in the mixing ratio 1:1 is spread on a paint card and measured. The mixture has a strong gold hue.

The measurement of the paint card gives the following values:

| a: 1.55 | b: 22.13 |
|---|---|

USE EXAMPLES

Example A1

Contouring Stick for the Face

| Ingredients | INCI (EU) | [%] |
|---|---|---|
| Red interference pigment according to Example 2 | CI 77891 (Titanium Dioxide), Mica, Tin Oxide | 5.00 |
| Green interference pigment according to Example 6 | CI 77891 (Titanium Dioxide), Mica, Tin Oxide | 5.00 |
| Blue interference pigment according to Example 4 | CI 77891 (Titanium Dioxide), Mica, Tin Oxide | 5.00 |
| Oxynex ® K liquid | PEG-8, TOCOPHEROL, ASCORBYL PALMITATE, ASCORBIC ACID, CITRIC ACID | 0.05 |
| Sensiva ® PA 20 | PHENETHYL ALCOHOL, ETHYLHEXYL GLYCERIN | 1.00 |
| Paraffin viscous | PARAFFINUM LIQUIDUM | 2.10 |
| Adeps Lanae | LANOLIN | 3.50 |
| Paracera C 44 | COPERNICIA CERIFERA CERA, CERESIN | 5.20 |
| Isopropyl myristate | ISOPROPYL MYRISTATE | 5.60 |
| Wax white | CERA ALBA | 8.75 |
| Fragrance | PARFUM | 0.20 |
| Castor oil | RICINUS COMMUNIS SEED OIL | to 100.00 |

Example A2

Medical Covering Ointment for Strong Hiding of Pigment/Age Spots

| Ingredients | INCI (EU) | [%] |
|---|---|---|
| Red interference pigment according to Example 2 | CI 77891 (Titanium Dioxide), Mica, Tin Oxide | 6.00 |
| Green interference pigment according to Example 6 | CI 77891 (Titanium Dioxide), Mica, Tin Oxide | 6.00 |
| Blue interference pigment according to Example 4 | CI 77891 (Titanium Dioxide), Mica, Tin Oxide | 6.00 |
| Oxynex ® K liquid | PEG-8, TOCOPHEROL, ASCORBYL PALMITATE, ASCORBIC ACID, CITRIC ACID | 0.05 |
| Sensiva ® PA 20 | PHENETHYL ALCOHOL, ETHYLHEXYL GLYCERIN | 1.00 |
| Paraffin viscous | PARAFFINUM LIQUIDUM | 2.10 |
| Adeps Lanae | LANOLIN | 3.50 |
| Paracera C 44 | COPERNICIA CERIFERA CERA, CERESIN | 5.25 |
| Isopropyl myristate | ISOPROPYL MYRISTATE | 5.60 |
| Wax white | CERA ALBA | 8.75 |
| Castor oil | RICINUS COMMUNIS SEED OIL | to 100.00 |

Example A3

Face Make Up with UV Protection and for Freshening Up the Complexion

| Ingredients | INCI (EU) | [%] |
|---|---|---|
| Red interference pigment according to Example 2 | CI 77891 (Titanium Dioxide), Mica, Tin Oxide | 7.50 |
| Green interference pigment according to Example 6 | CI 77891 (Titanium Dioxide), Mica, Tin Oxide | 2.50 |
| Blue interference pigment according to Example 4 | CI 77891 (Titanium Dioxide), Mica, Tin Oxide | 5.00 |

-continued

| Ingredients | INCI (EU) | [%] |
|---|---|---|
| Texapon K 12 P | SODIUM LAURYL SULFATE | 0.60 |
| Veegum | MAGNESIUM ALUMINUM SILICATE | 1.00 |
| 1,2-Propanediol | PROPYLENE GLYCOL | 10.00 |
| Eusolex ® OCR | OCTOCRYLENE | 2.00 |
| Parteck ® LUB STA 50 | STEARIC ACID | 1.50 |
| Eusolex ® 9020 | BUTYL METHOXYDIBENZOYL-METHANE | 0.50 |
| RonaCare ® AP | BIS-ETHYLHEXYL HYDROXYDIMETHOXY BENZYLMALONATE | 0.50 |
| Parteck ® LUB MST | MAGNESIUM STEARATE | 0.10 |
| Tego Care 450 | POLYGLYCERYL-3 METHYLGLUCOSE DISTEARATE | 3.50 |
| Eutanol G | OCTYLDODECANOL | 5.50 |
| Isopropyl myristate | ISOPROPYL MYRISTATE | 6.50 |
| Euxyl ® PE 9010 | PHENOXYETHANOL, ETHYLHEXYL GLYCERIN | 1.00 |
| Fragrance | PARFUM | 0.20 |
| Water, demineralized | AQUA | to 100.00 |

Example A4

Skin Elixir for Slight Freshening Up of Colour

| Ingredients | INCI (EU) | [%] |
|---|---|---|
| Red interference pigment according to Example 2 | CI 77891 (Titanium Dioxide), Mica, Tin Oxide | 1.00 |
| Green interference pigment according to Example 6 | CI 77891 (Titanium Dioxide), Mica, Tin Oxide | 2.00 |
| Blue interference pigment according to Example 4 | CI 77891 (Titanium Dioxide), Mica, Tin Oxide | 0.50 |
| Glycerol 85% | GLYCERIN, AQUA | 3.00 |
| Carbopol ® ETD 2020 | ACRYLATES/C10-30 ALKYL ACRYLATE CROSSPOLYMER | 0.20 |
| Cetiol OE | DICAPRYLYL ETHER | 3.00 |
| Crodamol ISIS-LQ-(MV) | ISOSTEARYL ISOSTEARATE | 2.50 |
| Tegosoft ® DC | DECYL COCOATE | 1.50 |
| Novemer EC-2 Polymer | SODIUM ACRYLATES/BEHENETH-25 METHACRYLATE CROSSPOLYMER, HYDROGENATED POLYDECENE, LAURYL GLUCOSIDE | 0.50 |
| Sodium hydroxide, 10% | AQUA, SODIUM HYDROXIDE | 0.00 |
| Water, demineralized | AQUA | to 100.00 |

Example A5

W/Si Liquid Foundation with UV Protection

| Ingredients | INCI (EU) | [%] |
|---|---|---|
| Red interference pigment according to Example 2 | CI 77891 (Titanium Dioxide), Mica, Tin Oxide | 3.00 |
| Green interference pigment according to Example 6 | CI 77891 (Titanium Dioxide), Mica, Tin Oxide | 3.00 |
| Blue interference pigment according to Example 4 | CI 77891 (Titanium Dioxide), Mica, Tin Oxide | 3.00 |
| Glycerol 85% | GLYCERIN, AQUA | 8.00 |
| Eusolex ® T-S | TITANIUM DIOXIDE (NANO), ALUMINA, STEARIC ACID | 8.50 |
| KF-6028 | PEG-9 POLYDIMETHYLSILOXYETHYL DIMETHICONE | 3.50 |
| KF-6038 | LAURYL PEG-9 POLYDIMETHYLSILOXYETHYL DIMETHICONE | 2.00 |
| USG-105 | DIMETHICONE/VINYL DIMETHICONE CROSSPOLYMER, METHYL TRIMETHICONE | 1.00 |
| TMF-1.5 | METHYL TRIMETHICONE | 17.00 |
| DM-Fluid-A-6cs | DIMETHICONE | 10.00 |
| Salacos 913 | ISOTRIDECYL ISONONANOATE | 4.00 |
| KF-56A | DIPHENYLSILOXY PHENYL TRIMETHICONE | 5.00 |
| Bentone 38 V | DISTEARDIMONIUM HECTORITE | 0.85 |
| KSP-100 | VINYL DIMETHICONE/METHICONE SILSESQUIOXANE CROSSPOLYMER | 2.50 |
| Water, demineralized | AQUA | to 100.00 |

Example A6

Face Powder for Balancing Out Slightly Yellowish Hues for Pale Asiatic Skin

| Ingredients | INCI (EU) | [%] |
|---|---|---|
| Red interference pigment according to Example 2 | CI 77891 (Titanium Dioxide), Mica, Tin Oxide | 1.00 |
| Blue interference pigment according to Example 4 | CI 77891 (Titanium Dioxide), Mica, Tin Oxide | 1.50 |
| Unipure Red LC 381 | CI 77491 | 0.22 |
| Unipure Brown LC 889 | CI 77491, CI 77499 | 0.35 |
| Parteck ® LUB MST | MAGNESIUM STEARATE | 2.40 |
| Eutanol G | OCTYLDODECANOL | 4.40 |
| Parteck ® LUB talc | TALC | to 100.00 |

Example A7

Face Powder for Balancing Out Slightly Yellowish Hues on Darker Skin Types

| Ingredients | INCI (EU) | [%] |
|---|---|---|
| Red interference pigment according to Example 2 | CI 77891 (Titanium Dioxide), Mica, Tin Oxide | 2.50 |
| Blue interference pigment according to Example 4 | CI 77891 (Titanium Dioxide), Mica, Tin Oxide | 2.50 |

-continued

| Ingredients | INCI (EU) | [%] |
|---|---|---|
| Unipure Red LC 381 | CI 77491 | 0.22 |
| Unipure Brown LC 889 | CI 77491, CI 77499 | 0.35 |
| Parteck ® LUB MST | MAGNESIUM STEARATE | 2.40 |
| Eutanol G | OCTYLDODECANOL | 4.40 |
| Parteck ® LUB talc | TALC | to 100.00 |

Example A8

Face Powder for Balancing Held Slightly Reddish Shades on Caucasian Skin Type

| Ingredients | INCI (EU) | [%] |
|---|---|---|
| Red interference pigment according to Example 2 | CI 77891 (Titanium Dioxide), Mica, Tin Oxide | 2.00 |
| Blue interference pigment according to Example 4 | CI 77891 (Titanium Dioxide), Mica, Tin Oxide | 0.50 |
| Unipure Red LC 381 | CI 77491 | 0.22 |
| Unipure Brown LC 889 | CI 77491, CI 77499 | 0.35 |
| Parteck ® LUB MST | MAGNESIUM STEARATE | 2.40 |
| Eutanol G | OCTYLDODECANOL | 4.40 |
| Parteck ® LUB talc | TALC | to 100.00 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A pigment mixture comprising two or three interference pigments which each have different interference colours, where the interference colours are selected from the colours red, blue and green and the CIE Lab* colour ranges of the individual pigments are defined as follows:
red interference pigment: a≥25 and b≥0
blue interference pigment: −20≤a≤40 and b≤−50
green interference pigment: a≤−15 and b≥0,
wherein the interference pigments are based on flake-form substrates and wherein said pigment mixture are suitable for cosmetics,
wherein the flake-form substrates are natural mica, synthetic mica, glass flakes, $SiO_2$ flakes, $Al_2O_3$ flakes or mixtures thereof,
wherein the interference pigments have a particle size of $D_{50}$<25 μm, and
wherein color intensity and hue of red/green/blue/gold of the pigment mixture is set solely by a mixing ratio of the two or three interference pigments.

2. A pigment mixture according to claim 1, wherein the CIE Lab* colour ranges of the individual pigments are defined as follows:
red interference pigment: a≥30 and b≥5
blue interference pigment: −15≤a≤30 and b≤−60
green interference pigment: a≤−20 and b≥15.

3. A pigment mixture according to claim 1, wherein the CIE Lab* colour ranges of the individual pigments are defined as follows:
red interference pigment: a≥35 and b≥5
blue interference pigment: −10≤a≤20 and b≤−65
green interference pigment: a≤−25 and b≥20.

4. A pigment mixture comprising
two or three interference pigments which each have different interference colours, where the interference colours are selected from the colours red, blue and green and the CIE Lab* colour ranges of the individual pigments are defined as follows:
red interference pigment: a≥25 and b≥0
blue interference pigment: −20≤a≤40 and b≤−50
green interference pigment: a≤−15 and b≥0
wherein the interference pigments are based on flake-form substrates and are suitable for cosmetics,
wherein the interference pigments are based on flake-form substrates,
wherein the flake-form substrates are natural mica, synthetic mica, glass flakes, $SiO_2$ flakes, $Al_2O_3$ flakes or mixtures thereof, and
wherein the interference pigments have a particle size of $D_{50}$<25 μm, and
wherein color intensity and hue of red/green/blue/gold of the pigment mixture is set solely by a mixing ratio of the two or three interference pigments.

5. A pigment mixture according to claim 4, wherein the flake-form substrates are natural and/or synthetic mica.

6. A pigment mixture according to claim 4, wherein the flake-form substrates are enveloped with a highly refractive interference layer having a refractive index of ≥1.8.

7. A pigment mixture according to claim 6, wherein the highly refractive layer is a $TiO_2$ layer or consists of a sequence of $TiO_2$—$SiO_2$—$TiO_2$.

8. A process for the preparation of the pigment mixture according to claim 1, wherein two or three interference pigments are mixed with one another.

9. A method comprising including a pigment mixture according to claim 1 in paints, coatings, printing inks, security printing inks, plastics, ceramic materials, glazes, glasses, and cosmetic formulations, and for the preparation of pigment preparations and dry preparations.

10. A method according to claim 9 wherein the pigment mixture is included in medical covering ointments, contour sticks, makeups, foundations and concealers.

11. A formulation comprising a pigment mixture according to claim 1.

12. A formulation according to claim 11, which comprises the pigment mixture and at least one constituent selected from absorbents, astringents, antimicrobial substances, antioxidants, antiperspirants, antifoaming agents, antidandruff active compounds, antistatics, binders, biological additives, bleaching agents, chelating agents, deodorising agents, emollients, emulsifiers, emulsion stabilisers, dyes, humectants, film formers, fillers, fragrances, flavours, insect repellents, preservatives, corrosion protection agents, cosmetic oils, solvents, oxidants, vegetable constituents, buffer substances, reducing agents, surfactants, propellant gases, opacifying agents, UV filters and UV absorbers, denaturing agents, aloe vera, avocado oil, coenzyme Q10, green tea extract, viscosity regulators, perfume and vitamins.

13. A pigment mixture according to claim 4, wherein the interference pigments have a particle size of $D_{50}$<25 μm.

14. A pigment mixture comprising two or three interference pigments which each have different interference colours, where the interference colours are selected from the colours red, blue and green and the CIE Lab* colour ranges of the individual pigments are defined as follows:
red interference pigment: a≥25 and b≥0 blue interference pigment: −20≤a≤40 and b≤−50
green interference pigment: a≤−15 and b≥0 and
wherein the interference pigments are based on flake-form substrates and have a particle size distribution, determined in accordance with Malvern, Mastersizer 2000, of $D_{10}$=<12 μm, $D_{50}$=<25 μm, $D_{90}$=<45 μm, and
wherein color intensity and hue of red/green/blue/gold of the pigment mixture is set solely by a mixing ratio of the two or three interference pigments.

15. A pigment mixture of claim 14 wherein the interference pigments have a particle size distribution, determined in accordance with Malvern, Mastersizer 2000, of $D_{10}$=<10 μm, $D_{50}$=<15 μm, $D_{90}$=<20 μm.

16. A pigment mixture of claim 14 wherein the interference pigments have a particle size distribution, determined in accordance with Malvern, Mastersizer 2000, of $D_{10}$=<7 μm, $D_{50}$=<12 μm, $D_{90}$=<17 μm.

* * * * *